US007816329B2

(12) United States Patent
Vila Pahi et al.

(10) Patent No.: US 7,816,329 B2
(45) Date of Patent: Oct. 19, 2010

(54) THERAPEUTIC USE FOR A GROUP OF SULPHATED POLYSACCHARIDES

(75) Inventors: Francisco Javier Vila Pahi, Barcelona (ES); Josep Escaich Ferrer, Barcelona (ES); August Lodewijk Verbruggen, Barcelona (ES); Josep Verges Milano, Corbera De Llobregat (ES); Ramon Ruhi Roura, Barcelona (ES); Carlos Raul Alaez Verson, Barcelona (ES)

(73) Assignee: Bioiberica, S.A., Barcelona (ES)

( * ) Notice: Subject to any disclaimer, the term of this patent is extended or adjusted under 35 U.S.C. 154(b) by 114 days.

(21) Appl. No.: 10/590,311

(22) PCT Filed: Feb. 11, 2005

(86) PCT No.: PCT/EP2005/001390

§ 371 (c)(1),
(2), (4) Date: Aug. 23, 2006

(87) PCT Pub. No.: WO2005/084610

PCT Pub. Date: Sep. 15, 2005

(65) Prior Publication Data

US 2008/0051350 A1 Feb. 28, 2008

(30) Foreign Application Priority Data

Feb. 27, 2004 (ES) ................................ 200400464

(51) Int. Cl.
*A61K 31/715* (2006.01)
(52) U.S. Cl. ........................................... 514/25; 514/54
(58) Field of Classification Search ................... 514/25, 514/54
See application file for complete search history.

(56) References Cited

U.S. PATENT DOCUMENTS

| 4,021,545 | A | | 5/1977 | Nair et al. | |
| 4,699,900 | A | | 10/1987 | Bayol et al. | |
| 5,145,841 | A | * | 9/1992 | Cullis-Hill et al. | ............ 514/54 |
| 2003/0181416 | A1 | | 9/2003 | Comper | |

FOREIGN PATENT DOCUMENTS

| EP | 0 561 379 A | 9/1993 |
| WO | WO-92/13541 A | 8/1992 |
| WO | WO-02/36132 A | 5/2002 |
| WO | WO-03/006645 A | 1/2003 |
| WO | WO-2005/054446 A | 6/2005 |

OTHER PUBLICATIONS

Dictionary.com, 2002, p. 3.*
Komai et al, International Journal of Biological Macromolecules, 2002, 30, 197-204.*
The Merck Manual, 16th Edition, 1992, pp. 1338-1342.*
Database CA Online!: Accession No. 1999-492587; Minami, S. et al., "Veterinary-clinical uses of curdlan sulfate," XP002347885, Chemical Abstracts Service, Columbus, Ohio (1999).
Miyamoto, K. et al., "Novel plasma-separation dilayer gellan-gellan-sulfate adsorber for direct removal of extra domain A containing fibronectin from the blood of rheumatoid arthritis patients," International Journal of Biological Macromolecules, vol. 30, No. 3-4, pp. 197-204 (2002).
Jordan, K.M. et al., EULAR Recommendations 2003: An Evidence Based Approach to the Management of Knee Osteoarthritis: Report of a Task Force of the Standing Committee for International Clinical Studies Including Therapeutic Trials (ESCISIT); *Ann Rheum Dis.* 2003; 62, 1145-1155.
Altman, R. et al., "Development of Criteria for the Classification and Reporting of Osteoarthritis", *Arthritis and Rheumatism*, vol. 29, No. 8, Aug. 1986, pp. 1039-1049.
Klippel, John H. et al., "Osteoarthritis and Related Disorders", *Pheumatology*, $2^{nd}$ Ed., 1997.
Lequesne, M., "Symptomatic Slow-Acting Drugs in Osteoarthritis: A Novel Therapeutic Concept?*", *Expansion Scientifique Francaise*, 1994, 69-73.
Harris, Edward D., Rheumatoid Arthritis, "Pathophysiology and Implications of Therapy", *The New England Journal of Medicine*, vol. 322, No. 18, May 3, 1990, pp. 1277-1289.
Hochberg, Marc C., "Adult and Juvenile Rheumatoid Arthritis: Current Epidemiologic Concepts", *Epidemiologic Reviews—The Johns Hopkins University School of Hygiene and Public Health*, vol. 3, 1981, pp. 27-44.
Committee for Proprietary Medicinal Products (CPMP), "Points to Consider on Clinical Investigation of Medicinal Products Other than NSAIDS for Treatment of Rheumatoid Arthritis", *The European Agency for the Evaluation for Medicinal Products*, London, Dec. 17, 2003.
Combe, Bernard et al., "Euler Recommendations for the Management of Early Arthritis: Report of a Task Force of the European Standing Committee for International Clinical Studies Including Therapeutics (ESCISIT)", *Ann Rheum Dis.*, ARD Online First, published Jan. 5, 2006, www.ard.bmjjournals.com, pp. 1-24.
Gust Verbruggen et al., "Influence of Polysulfated Polysaccharides on Aggrecans Synthesized by Differentiated Human Articular Chondrocytes", The Journal of Rheumatology, 1999, 26:1663-1671.
Peter Ghosh, "The Pathobiology of Osteoarthritis and the Rationale for the Use of Pentosan Polysulfate for It's Treatment", Seminars in Arthritis and Rheumatism, 1999, 28(4):211-267.

* cited by examiner

*Primary Examiner*—Shaojia Anna Jiang
*Assistant Examiner*—Ganapathy Krishnan
(74) *Attorney, Agent, or Firm*—Sughrue Mion, PLLC

(57) ABSTRACT

The present invention relates to the use of a sulphated polysaccharide in acid form or as a physiologically acceptable salt thereof, selected from the group constituting of inulin sulphate, gellan sulphate, pullulan sulphate, curdlan sulphate, alginiq acid sulphate, laminarin sulphate, and pectin sulphate, for the preparation of a medicament for the treatment or prophylaxis of arthrosis in a mammal. Preferably, the sulphated polysaccharide is inulin sulphate, most preferably inulin polysulphate sodium salt. The present invention also relates to the use of a sulphated oligosaccharide derived from a polysaccharide selected from the group consisting of inulin, gellan, pullulan, curdlan, alginic acid, laminarin, and pectin, for the preparation of a medicament for the treatment or prophylaxis of arthrosis in a mammal.

11 Claims, 1 Drawing Sheet

THERAPEUTIC USE FOR A GROUP OF SULPHATED POLYSACCHARIDES

TECHNICAL FIELD OF THE INVENTION

The present invention relates to the use of a sulphated polysaccharide for the preparation of a medicament for the treatment or prophylaxis of arthrosis. Likewise, the present invention relates to the use of a sulphated oligosaccharide for the preparation of a medicament for the treatment or prophylaxis of arthrosis.

DESCRIPTION OF THE PRIOR ART

Arthrosis, also known as osteoarthritis, is a degenerative joint disease which affects most people over 65 years of age, characterised by a gradual degradation of the cartilaginous tissue, together with the presence of inflammation and pain. Inflammation appears especially when the disease is in an advanced stage and is different in nature from the inflammation observed in rheumatoid arthritis, and generally is only a minority component of arthrosic disease. Arthrosis may be defined as the degeneration of the hyaline articular cartilage. A secondary effect thereto is affectation of the sinovial membrane and the subchondral bone, as well as the formation of new bone on the margins of the joint surfaces. The etiology of arthrosis is unknown and its evolution is slow.

The cartilage allows bones to move, slipping over one another. It also absorbs the stress produced by physical movement. In arthrosis, the surface of the cartilage breaks and wears out, causing bones to move against one another, which leads to friction, pain, swelling, and loss of joint movement. As time goes on, the joint may deform.

As an aid in the diagnosis of arthrosis, two techniques are mainly used: X-rays, which is the simplest method to identify the bone changes in the joint, and nuclear magnetic resonance (NMR), which, unlike the former, makes it possible to simultaneously view all the joint's components.

Under normal conditions, cartilage renewal is a very slow process, which consists of a constant synthesis (anabolism) and degradation (catabolism) of the extracellular matrix components. The chondrocyte is the cell responsible for this metabolism, which must be coordinated.

Under pathological conditions, this process is altered, because cartilage renewal is accelerated, which leads to a precocious repair of the cartilaginous tissue caused by an imbalance between the chondrocyte's anabolic and catabolic programmes, which entails degradation of the cartilage. The repair reaction is the result of a hyperproliferation of chondrocytes, jointly with an increase in the synthesis of the cartilage's extracellular matrix components by these cells (D. Hamermam et al., *N. Engl. J. Med.*, 320, 1322-1330 (1989)). Consequently, there exists a balance between synthesis and degradation of the cartilage which controls said homeostatic reaction and which depends on systemic hormones and growth factors whose secretions decrease with age. Cartilage degradation is regulated by enzymes and free radicals produced by adjacent tissues, but also by the chondrocyte itself.

We will highlight the following current pharmacological treatments for arthrosis:

Symptomatic-action substances which have a rapid action, such as analgesics, non steroidal anti-inflammatory drugs (NSAIDs), corticoids, and cyclo-oxygenase 2 inhibitors (COX-2).

Symptomatic-action substances which act in a slower manner, known as SYSADOA (Symptomatic Slow Acting Drug for Osteoarthritis) (M. G. Lequesne, *Rev. Rhum.* (Eng./Ed.), 61, 69-73 (1994)), which include hyaluronic acid, chondroitin sulphate, and glucosamine sulphate. This group is characterised in that the effect starts after 2-3 weeks of treatment and persist for 2 to 6 months after administration ceases.

Documents have been found in the literature about other applications for the sulphated polysaccharides of the present invention:

R. V. Jones (U.S. Pat. No. 2,686,779) discloses a procedure to prepare inulin sulphate salts with alkaline metals. In said patent it is stressed that inulin sulphate alkaline salts with various degrees of sulphation have been applied in the chemical industry as paste thickeners, adhesives, and mud additives used in oil well drilling.

It has been described that inulin sulphate exhibits anti-coagulant (*Arkiv for kemi, mineralogi o. geologi., Bd* 248 (5), 1-4 (1946)) and antilipemic activity (*Arch. Int. Pharmacodyn, XCIX*, 334 (1954)).

V. G. Nair et al. (U.S. Pat. No. 4,021,545) reveal that inulin polysulphate salts (completely sulphated) have a complement-inhibiting activity, such that, according to the inventors, they could be used in the treatment of diseases such as rheumatoid arthritis, systemic erythematous lupus, certain types of vasculitis, etc.

G. Franz et al. (*Bioactive Carbohydrate Polymers*, 47-58, Kluwer Academic Publishers, Netherlands, 2000) describe pullulan sulphate's anti-coagulant and anti-thrombotic activity.

C. C. Lee (EP 499.164) claims, albeit without describing it in any example, an injectable composition which may contain carrageenan in order to supplement natural lubricating fluids. In the cited document they do not mention carrageenan polysulphate.

T. Kanamaru et al. (U.S. Pat. No. 5,135,920) disclose that curdlan sulphate is an angiostatic agent. S. Alban et al. (*Thromb. Res.* 78 (3), 201-10 (1995)) describe that the same compound acts as an anti-coagulant and anti-thrombotic agent.

T. Hata et al. (JP 04257509) show the application of alginic acid sulphate as a moisturising agent in cosmetic preparations. L. Lange et al. (ES 2.064.736) describe the use of alginate sulphate to inhibit pancreatic cholesterol.

E. Besterman (*Brit. Med. J.*, 310 (1957, I)) describes that the polysaccharide laminarin sulphate exhibits antilipemic activity. H. Q. Miao et al. (*Int. J. Cancer,* 83 (3), 424-31 (1999)) reveal laminarin sulphate's anti-metastatic activity. P. Bohlen et al. (WO 03/006645) describe that the polysaccharide laminarin sulphate inhibits heparanase activity, which, as they claim, is associated, among others, to inflammatory processes, diabetes, or arthritis.

L. Lange et al. (ES 2.064.736) reveal that the polysaccharide pectin sulphate is useful for treating high blood cholesterol levels.

Until now no description has been found of the use of inulin sulphate, gellan sulphate, pullulan sulphate, curdlan sulphate, alginic acid sulphate, laminarin sulphate, or pectin sulphate with any degree of sulphation, or of carrageenan polysulphate in the treatment or prophylaxis of arthrosis.

We also have not found thus far any description of the use of the sulphated oligosaccharides corresponding to the above-mentioned sulphated polysaccharides in the treatment or prophylaxis of arthrosis.

From all of the foregoing we may conclude that providing a useful drug for the treatment of arthrosis is still a therapeutic problem.

DISCLOSURE OF THE INVENTION

The problem to be solved by this invention is to provide alternative sulphated polysaccharides to be used in the treatment or prophylaxis of arthrosis. The solution corresponding to the first aspect of the invention refers to the use of a sulphated polysaccharide in acid form or as a physiologically acceptable salt thereof, selected from the group consisting of inulin sulphate, gellan sulphate, pullulan sulphate, curdlan sulphate, alginic acid sulphate, laminarin sulphate, and pectin sulphate, for the preparation of a medicament for the treatment or prophylaxis of arthrosis in a mammal.

In a preferred embodiment, the sulphated polysaccharide is selected from the group consisting of inulin sulphate, gellan sulphate, pullulan sulphate, and curdlan sulphate. Among these, the most preferred are inulin sulphate and gellan sulphate.

In a more preferred embodiment, the sulphated polysaccharide is totally or partially salified with an alkaline or alkaline earth metal. Preferably, the alkaline metal is sodium and the preferred polysaccharide is inulin sulphate sodium salt. The polysaccharide gellan sulphate sodium salt is equally preferred.

Inulin sulphate sodium salt with a degree of sulphation between 25% and 62%, on anhydrous base, is more preferred.

Inulin sulphate sodium salt with a degree of sulphation between 55% and 62%, on anhydrous base, is even more preferred.

In another equally preferred embodiment, the sulphated polysaccharide is partially hydrolysed.

In another equally preferred embodiment, the sulphated polysaccharide is a polysulphated polysaccharide, selected from the group consisting of inulin polysulphate, gellan polysulphate, pullulan polysulphate, curdlan polysulphate, alginic acid polysulphate, laminarin polysulphate, and pectin polysulphate. Among these, the most preferred one is inulin polysulphate, preferably inulin polysulphate sodium salt. Equally preferred is gellan polysulphate, preferably gellan polysulphate sodium salt.

Another aspect of this invention is the use of carrageenan polysulphate for the preparation of a medicament for the treatment or prophylaxis of arthrosis in a mammal.

Another aspect of this invention is the use of a sulphated oligosaccharide in acid form or as a physiologically acceptable salt thereof, derived from a polysaccharide selected from the group consisting of inulin, gellan, pullulan, curdlan, alginic acid, laminarin, and pectin, for the preparation of a medicament for the treatment or prophylaxis of arthrosis in a mammal. Preferably, the sulphated oligosaccharide is derived from inulin. Also preferably, the sulphated oligosaccharide is derived from gellan.

In a preferred embodiment, the sulphated oligosaccharide is a polysulphated oligosaccharide.

Another aspect of this invention is the use of a sulphated oligosaccharide in acid form or as a physiologically acceptable salt thereof, produced by chemical synthesis, whose structure corresponds to a portion of the structure of a sulphated polysaccharide selected from the group consisting of inulin sulphate, gellan sulphate, pullulan sulphate, curdlan sulphate, alginic acid sulphate, laminarin sulphate, and pectin sulphate, for the preparation of a medicament for the treatment or prophylaxis of arthrosis in a mammal.

In an especially preferred embodiment, the medicament is adapted for oral administration.

Likewise, in an especially preferred embodiment, the drug is adapted for intra-articular administration.

The sulphated polysaccharides in this invention are well-known, and may be produced by partial or total sulphonation of the free hydroxyl groups present in the polysaccharides' structure: inulin, gellan, pullulan, curdlan, alginic acid, laminarin, and pectin. Carrageenan polysulphate is produced by total sulphonation of the free hydroxyls present in carrageenan.

Sulphonation of a hydroxyl group gives rise to the corresponding sulphate group.

Carrageenan already contains some sulphate groups within its structure. In this invention, carrageenan polysulphate is used.

When we speak herein about the degree of sulphation, this refers to the % of sulphate groups on an anhydrous base (with respect to the molecule).

When in the specification of the present invention we speak about sulphated polysaccharides, this relates to a sulphated polysaccharide with any degree of sulphation. In the literature, a sulphated polysaccharide with a high degree of sulphation is usually called a polysulphated polysaccharide and, naturally, when the polysaccharide is totally sulphated it is also called a polysulphated polysaccharide. Consequently, the present invention includes polysulphated polysaccharides (inulin polysulphate, carrageenan polysulphate, gellan polysulphate, pullulan polysulphate, curdlan polysulphate, alginic acid polysulphate, laminarin polysulphate, and pectin polysulphate).

Sulphated polysaccharides may be produced by partial or total sulphonation of the free hydroxyls in the above-mentioned commercial polysaccharides, by means of procedures described in the literature, such as, for example, by means of chlorosulphonic acid/pyridine (T. Astrup et al., *Acta Physiol. Scand.*, 8, 215-226 (1944)), or else using piperidine-N-sulphonic acid (N. Kinzo et al., *Carbohyd. Res.*, 21, 420-426 (1972)), or else using the sulphur trioxide-pyridine complex (C. Mähner et al., *Carbohyd. Res.*, 331, 203-208 (2001)).

In order to produce various degrees of sulphation, the above-mentioned procedures may be modified (changing the reagent concentrations, the reaction temperature, reaction times, etc. . . . ). Also, if so desired, different polysaccharide hydroxyls may be selectively sulphonated, by means of protection/deprotection of the polysaccharide hydroxyls.

If the starting polysaccharide's average molecular weight is too high, it can, if so desired, be partially hydrolysed before or after sulphonation.

The sulphated oligosaccharides used in the invention may be produced by enzymatic or chemical hydrolysis (procedures which are well-established in the literature) of the commercial polysaccharide, followed by sulphonation, or else directly by enzymatic or chemical hydrolysis of the sulphated polysaccharide. They may also be produced by chemical synthesis.

When we speak in the specification of the present invention about a physiologically acceptable salt, this refers to a salt of an alkaline metal, such as for example sodium or potassium, a salt of an alkaline-earth metal, such as for instance calcium or magnesium, or else an organic salt, such as for instance salt with trimethylamine, with triethylamine, or with an amino acid, such as for instance lysine, arginine, proline, glycine, or serine.

Salification of the sulphated polysaccharide may be performed by simple, well-known chemical procedures.

For use in the treatment or prevention of arthrosis, the sulphated polysaccharides of the invention, whether in acid form or as a physiologically acceptable salt thereof, are formulated in appropriate pharmaceutical compositions, using conventional techniques and excipients or carriers, such as the ones described in *Remington's Pharmaceutical Sciences Handboock*, Mack Pub. Co., N.Y., USA.

The pharmaceutical compositions of the invention may be administered to the patient in required doses. Administration of the compositions may be performed by various means, for example, oral, intravenous, intra-peritoneal, intra-articular, subcutaneous, intramuscular, topical, sublingual, intradermal, or intranasal. The pharmaceutical compositions of the invention include a therapeutically effective quantity of the sulphated polysaccharide in this invention, in acid form or as a physiologically acceptable salt thereof, with said quantity being dependent on many factors, such as for example, the patient's physical condition, age, sex, specific compound, means of administration, and other factors well-known in technology. Furthermore, it is understood that said dosage of the active compound may be administered in single- or multiple-dose units in order to provide the desired therapeutic effects. If so desired, other therapeutic agents may be used jointly with the ones provided by this invention.

In general, the pharmaceutical preparations in the invention will be in solid or liquid form, or in the form of a gel. The solid-form pharmaceutical preparations which may be prepared in accordance with this invention include powders, minigranules (pellets), pills, dispersible granules, capsules, suppositories, and other solid galenical forms. The liquid-form preparations include solutions, suspensions, emulsions, and microspheres. Preparations in solid form which, immediately before being used, may be converted to liquid preparations for oral, parenteral, or intra-articular administration, are also contemplated. Said liquid forms include solutions, suspensions, and emulsions.

DETAILED DESCRIPTION OF THE INVENTION

Figure 1:
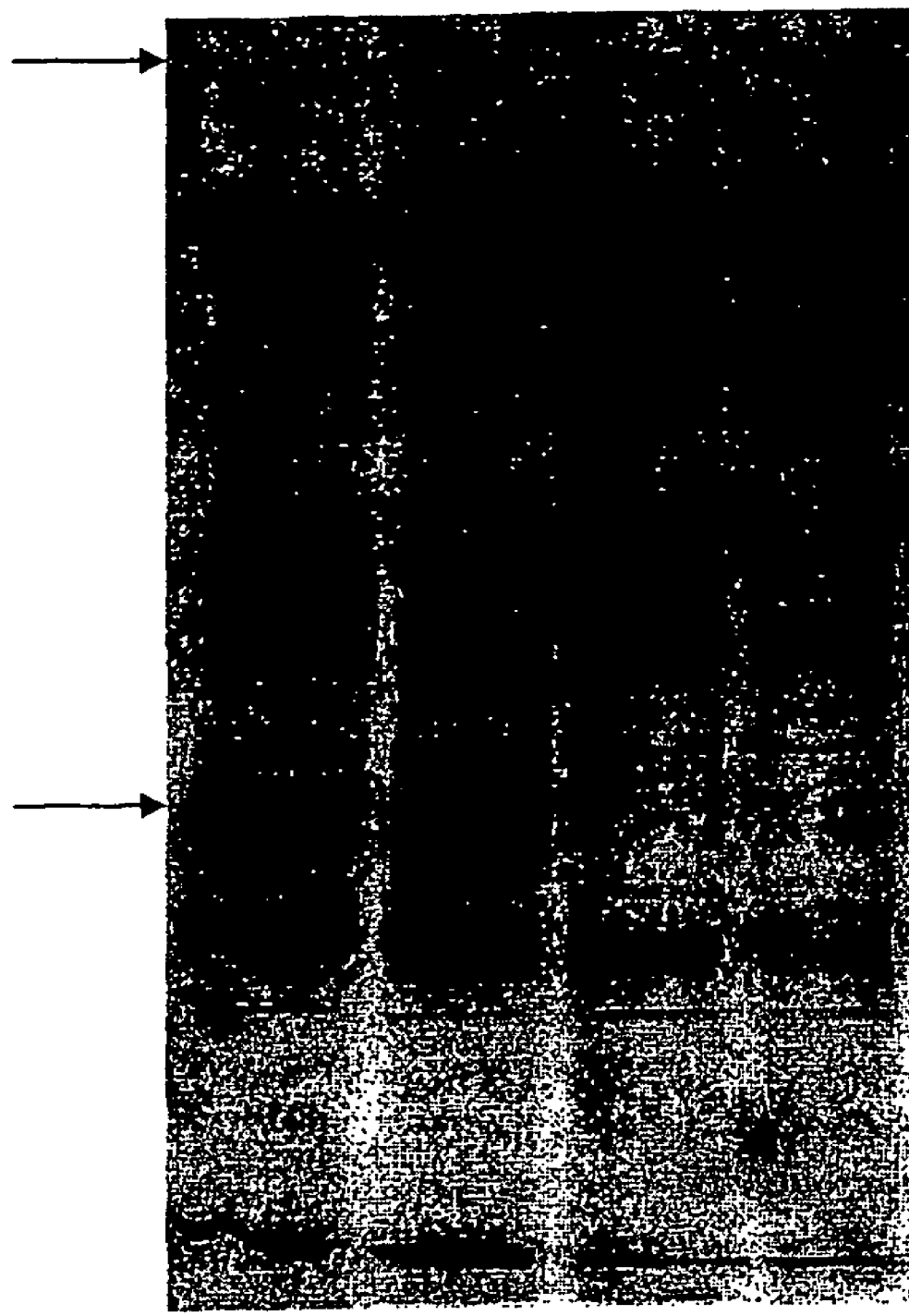
FIG. 1 represents a Western Blott. The upper arrow indicates the area of intact aggrecan and the lower arrow indicates the area of aggrecan fragments labelled with antibody NITGE G1. In the first of the wells a control sample was seeded (without any treatment); in the second one, a sample treated with interleukin-1 (IL-1α); in the third, a sample treated with 100 μg/mL of inulin polysulphate in Chemical Example 1, and, in the fourth, a sample treated with IL-1 and 100 μg/mL of inulin polysulphate in Chemical Example 1.

The following examples are merely illustrative and do not represent a limitation on the scope of this invention.

CHEMICAL EXAMPLE

Example 1

Preparation of Inulin Polysulphate Sodium Salt

Under constant stirring, at a temperature<6° C., 88 mL (1.32 mol; 1.8 eq/OH) of chlorosulphonic acid were added drop by drop to 580 mL (7.20 mol) of dry pyridine. The resulting mixture was heated to 75° C. and, subsequently, 40 g (0.25 mol) of inulin (Fibruline Standar, marketed by Trades S.A.) were added. The stirring and the heating to 100° C. were continued for 5 h. Once this time elapsed, the reaction mixture was allowed to cool down to approximately 50° C. and 50 mL of de-ionised water were added in order to destroy the chlorosulphonic acid excess. During this step, the ambient temperature was slightly increased and two phases appeared.

The crude reaction product was allowed to rest until it reached ambient temperature. The upper phase (pyridine) was separated by suction, while the oily lower phase was poured over a 10% solution of sodium acetate in methanol. The precipitate that was formed was allowed to sediment. The supernatant was separated by decanting and discarded.

Treatment with the sodium acetate methanolic solution was repeated twice and, in the last step, the solid was separated by vacuum filtering by means of a type k-100 depth filter (Pall Corporation. Seitz-k-100).

The filter produced (brown solid) was dissolved in distilled water and the resulting solution was vacuum filtered by means of a k-100 depth filter in order to eliminate the insoluble matter remainders resulting from the reaction.

The filtrate resulting from the preceding step was a dark amber colour solution which was treated with quaternary ammonium (Quartamin). As a consequence, a very abundant solid was formed which was isolated by vacuum filtering using a Hyflo earth pre-layer (100 g). The filter was abundantly washed with distilled water The inulin polysulphate-Quartamin complex was carefully separated from the filtering earths and treated with a 20% NaCl aqueous solution, at 80° C., for two hours.

Once the two hours of reaction elapsed, the heating was stopped, and when the ambient temperature reached 60° C., isopropanol was added. Stirring was maintained for 30 min. and, subsequently, the mixture was poured into a decanting funnel in order to separate the aqueous phase from the organic one.

The organic phase (isopropanol+quaternary ammonium) was discarded. The aqueous phase was vacuum filtered in order to eliminate the Hyflo earth remainders.

A mixture of methanol/acetone was poured over the aqueous phase. The brown precipitate that was formed was allowed to sediment. The supernatant was separated by decanting and discarded. The sediment was washed with methanol and subsequently dissolved in de-ionised water.

The pH of the resulting solution was adjusted between 10.5-11 with 10% NaOH. The solution was heated to 50° C. and treated with $H_2O_2$ for 15 min. Finally, the heating was stopped and the pH of the medium was adjusted to 5.5 with a 2% acetic acid solution.

When the discoloured solution reached ambient temperature, a 10% methanol/sodium acetate solution was poured thereon. A white or slightly yellow precipitate immediately formed which was allowed to sediment.

The supernatant was separated by decanting and the sediment was abundantly anhydrated with methanol.

The inulin sulphate was separated by vacuum filtering with a No. 3 porous plate and dried in a vacuum heater at 30° C. until the methanol concentration was equal to or lower than 0.3%.

The product was produced in the form of a fine, amorphous powder, white or slightly yellow in colour.

Determination of the Degree of Sulphation (Organic Sulphates) in the Produced Inulin Polysulphate Sodium Salt Exactly 150 mg of the product were weighed, they were dissolved in water, and the resulting solution was taken to 250 mL with the same solvent. 5 mL of this solution were pipetted, they were transferred to a 50 mL beaker, and 25 mL of water were added. It was photometrically assessed at 420 nm, with a 0.1% (0.00279 M) N-cetylpyridinium chloride (CPC) solution.

The sulphate content was calculated using the following equation:

$$\% \, SO_4 = \frac{V \times 0.00279 \times 96 \times 100}{\frac{5 \times (100 - PPS) \times W}{250 \times 100}} = \frac{13.392 \times V \times 100}{\frac{100 - PPS}{100} \times W}$$

Where:
V: Volume of the 0.1% CPC solution consumed, in mL. 0W: Weight of the sample, in mg.
PPS: Weight loss by desiccation of the product (105° C., 4 h), in %.
Degree of sulphation produced: 58.0%, expressed on anhydrous base, which corresponds to a completely sulphated inulin molecule (sulphonation of all the hydroxyls)
Free residual pyridine and pyridine in salt form: 127 ppm (the permitted limit is 200 Ppm)
Free sulphates: 0.08%
IR (KBr) cm$^{-1}$: 2900 (C—O—H), 1247 (S=O), 800 (C—S—O)

PHARMACOLOGICAL EXAMPLES

The cartilage's resistance and repair capacity are determined by the proteoglycans of the extracellular matrix, particularly the aggrecans. Synthesis of these aggrecans by the articular chondrocytes, and their quality, diminishes with age, which is one of the main factors involved in the development of arthrosis.

Example 1

Evaluation of the In Vitro Effects of Inulin Polysulphate on the Synthesis of Extracellular Aggrecans in a Primary Culture of Human Chondrocytes This procedure may be applied to the evaluation of any sulphated polysaccharide of this invention.

1A: Aggrecan Levels Determined by the Incorporation of $^{35}$S

Materials and Methods

Human articular chondrocytes were isolated following the methods described by W. T. Green Jr. (*Clin. Orthop.*, 75, 248-260 (1971)) and K. E. Kuettner et al. (*J. Cell. Biol.*, 93, 743-750 (1982)).

These chondrocytes were cultured in an agarose gel following the method described by P. D. Benya et al. (*Cell*, 30, 215-224, (1982)), and modified by G. Verbruggen et al. (*Clin. Exp. Rheumatol.*, 8, 371-378 (1990)) and by M. Cornelissen et al. (*J. Tiss. Cult. Meth.*, 15, 139-146 (1993)).

The synthesis of aggrecans was determined by the incorporation of $^{35}$S, using labelled sodium sulphate Na$_2$$^{35}$SO$_4$ as radioactive precursor. After two weeks of culture, 10 µCi/mL of radio-labelled precursor were introduced in the culture medium for 48 h, as was the compound to be assayed (inulin polysulphate in Chemical Example 1) at different concentrations (0.0, 0.1, 0.5, 1.0, 5.0 µg/mL).

The synthesised $^{35}$S aggrecans once again partially accumulated in the intercellular agarose matrix or else were released in the incubation medium.

Once the incubation period ended, the agarose gel was mechanically broken down and subsequently digested by means of 3 mL of a 50 U/mL agarose solution in a 0.067 M phosphate buffer, at pH 6.0, in the presence of proteinase inhibitors.

The suspension thus produced was centrifuged; the supernatant containing the inter-territorial matrix's $^{35}$S aggrecans and the incubation medium containing the $^{35}$S aggrecan metabolites released in the extracellular matrix were subsequently united by means of chromatography.

The residue, which contained the chondrocytes and the associated $^{35}$S aggrecans, was treated for 48 hours with 1 mL of a 4.0 M guanidium chloride solution in a 0.05M acetate buffer at pH 5.8 containing the proteinase inhibitors.

The purpose of this operation is to extract the $^{35}$S aggrecans associated with the cells. The solution produced was centrifuged in order to separate the cells from the supernatant, which was subsequently separated by means of chromatography. The chromatography operations for the different fractions produced were performed on Sephadex G25 gel in a phosphate buffer pH 6.8 containing 0.01 M of Na$_2$SO$_4$, in order to separate the $^{35}$S aggrecans from the free Na$_2$$^{35}$SO$_4$.

The radioactivity of each of the macromolecular eluants produced was measured and related to the number of chondrocytes contained in the initial culture, expressed in pg of $^{35}$SO$_4$ incorporated into the aggrecans, per million chondrocytes per hour.

Results

They are shown in Tables 1, 2, and 3.

The tables show the remarkable effectiveness of the inulin polysulphate in Chemical Example 1, in the total production of re-synthesised aggrecans (Table 3). The inulin polysulphate in Chemical Example 1 is also capable of increasing production of aggrecans in the inter-territorial matrix (Table 1) as well as of the aggrecans associated with the cells (Table 2).

The optimum activity is found at a concentration of about 0.5 µg/mL.

TABLE 1

| pg $^{35}$S/10$^6$ cells/h | % change | % Total | IPS (µg/mL) |
| --- | --- | --- | --- |
| 7,710 |  | 67.4 | 0.0 |
| 7,818 | 1.4 | 66.2 | 0.1 |
| 12,383 | 60.6 | 70.7 | 0.5 |
| 10,887* | 41.2* | 70.7 | 1.0 |
| 8,340 | 8.2 | 67.9 | 5.0 |

Quantity of radioactively-labelled sulphur incorporated into the inter-territorial matrix's aggrecans, per million cells per hour.
% Change = Percentage change with respect to the untreated control (IPS = 0.0 µg/mL).
% Total = Percentage with respect to the total quantity of aggrecans.
IPS: dose of inulin polysulphate in Chemical Example 1 added.
*p < 0.05 with respect to the non-treated control.

TABLE 2

| pg $^{35}$S/10$^6$ cells/h | % change | % Total | IPS (µg/mL) |
| --- | --- | --- | --- |
| 2,378 |  | 20.9 | 0.0 |
| 2,737 | 15.1 | 23.5 | 0.1 |
| 3,064* | 28.8* | 18.4 | 0.5 |
| 2,662 | 11.9 | 17.9 | 1.0 |
| 2,041 | 14.2 | 17.4 | 5.0 |

Quantity of radioactively-labelled sulphur incorporated into the aggrecans of the inter-territorial matrix associated with the cells, per million cells per hour.
% Change = Percentage change with respect to the non-treated control (IPS = 0.0 µg/mL).
% Total = Percentage with respect to the total quantity of aggrecans.
IPS: dose of inulin polysulphate in Chemical Example 1 added.
*p < 0.05 with respect to the non-treated control.

TABLE 3

| pg $^{35}$S/10$^6$ cells/h | % change | % Total | IPS (μg/mL) |
|---|---|---|---|
| 11,429 |  | 100 | 0.0 |
| 11,756 | 2.9 | 100 | 0.1 |
| 17,312* | 51.5* | 100 | 0.5 |
| 15,281* | 33.7* | 100 | 1.0 |
| 12,106 | 3.0 | 100 | 5.0 |

Quantity of radioactively-labelled sulphur incorporated into the re-synthesised aggrecans, per million cells per hour.
% Change = Percentage change with respect to the non-treated control (IPS = 0.0 μg/mL).
% Total = Percentage with respect to the total quantity of aggrecans.
IPS: dose of inulin polysulphate in Chemical Example 1 added.
*p < 0.05 with respect to the non-treated control.

1B: Aggrecan Levels Determined by Means of Immunocytochemistry

Materials and Methods

The human articular chondrocytes were isolated and cultured following the previously described methods.

The accumulation of aggrecans associated with the chondrocytes was measured, after a week of culture, by means of the immunocytochemistry technique described by L. Wang et al. (*Osteoarthritis Cart.*, 9, 248-260 (2001)). The chondrocytes were treated with interleukin-1 (IL-1) in order to simulate a situation of inflammation and catabolism. The inulin polysulphate in Chemical Example 1 was added jointly with IL-1.

Once the incubation period ended, the chondrocytes were released from the agarose gel following the described method. The chondrocytes and the associated aggrecans were studied by means of flux cytometry using monoclonal antibodies specifically directed against the aggrecans' proteic part.

Results

They are shown in Table 4.

This Table confirms the effectiveness of the inulin polysulphate in Chemical Example 1 on the production of aggrecans associated with the cells.

Moreover, it can be seen that there is a dose-effect relationship, since, with greater doses of the compound, there is a greater increase in the production of aggrecans associated with the cells.

TABLE 4

|  | Donor M32 | | Donor F45 | |
|---|---|---|---|---|
|  | M ± SD | % Change | M ± SD | % Change |
| Control | 18.9 ± 0.2 | 105.6 | 36.5 ± 0.2 | 201.7 |
| IL-1 | 17.9 ± 0.3 | 100.0 | 18.1 ± 0.2 | 100.0 |
| IL-1 + IPS (0.5 μg/mL) | — | — | 20.4 ± 0.2* | 112.7* |
| IL-1 + IPS (1.0 μg/mL) | 20.8 ± 1.2* | 116.2* | 26.6 ± 0.1* | 147.0* |
| IL-1 + IPS (2.5 μg/mL) | 21.6 ± 1.1* | 120.7* | 39.0 ± 0.2* | 215.5* |
| IL-1 + IPS (5.0 μg/mL) | 25.0 ± 1.4* | 139.7* | — | — |

Mean fluorescence intensity in the chondrocytes after labelling of aggrecan with antibodies conjugated with fluorescein.
M ± SD = mean ± standard deviation.
% Change = Percentage change with respect to the group treated with IL-1.
IL-1 = Interleukin-1.
IPS = inulin polysulphate in Chemical Example 1.
*p < 0.05 with respect to the group treated with IL-1.

Example 2

In Vitro Effect of Inulin Polysulphate on the Synthesis of Aggrecans in a Rat Chondrosarcoma Chondrocyte Culture This procedure may be applied to the evaluation of any sulphated polysaccharide of this invention.

Materials and Methods

Rat chondrosarcoma chondrocyte cultures were set in 24-well plates and allowed to grow until they reached 80% confluence in DMEM medium (Dulbecco's Modification of Eagle's Medium) (+4.5 g/l of glucose)+10% bovine fetal serum (FCS).

Subsequently, the culture medium was removed and replaced by 1 ml of DMEM (+4.5 g/l of glucose)+10% FCS+ 20 μCi/ml $^{35}$S (Na$_2$$^{35}$SO$_4$) and 1, 10, and 100 μg/ml of inulin polysulphate in Chemical Example 1. Incorporation was facilitated for 18 hours and was subsequently finalised by the addition of solid guanidine HCl.

The macromolecules solubilised by guanidine HCl were separated from the non-incorporated isotopes by means of chromatography and the radioactivity was determined by means of a scintillation counter.

Results

They are shown in FIG. 1, where a Western Blott is represented which is the result of the various treatments applied to a rat chondrosarcoma chondrocyte culture. In said FIGURE, it may be seen that treatment of the chondrocytes with IL-1 causes an increase in aggrecan degradation, such that the band of aggrecan fragments labelled with antibody NITGE G1 becomes thicker. On the contrary, when the culture is treated with inulin polysulphate in Chemical Example 1, in the presence or not of IL-1, aggrecan degradation is inhibited, such that the above-mentioned band narrows down until it almost disappears. Consequently, inulin polysulphate is capable of reducing the aggrecan degradation in a chondrocyte culture, for which reason it will also stop the degradation of the extracellular matrix in the case of patients with arthrosis.

The invention claimed is:

1. A method for the treatment of osteoarthritis, comprising administering orally to a mammal in need thereof a therapeutically effective amount of inulin sulphate in acid form or as an alkaline metal salt or an alkaline earth metal salt thereof.

2. The method according to claim 1, wherein the alkaline metal salt of inulin sulphate is inulin sulphate sodium salt.

3. The method according to claim 2, wherein the inulin sulphate sodium salt exhibits a degree of sulphation between 25% and 62%, on an anhydrous basis.

4. The method according to claim 3, wherein the degree of sulphation is between 55% and 62%, on an anhydrous basis.

5. The method according to claim 4, wherein the degree of sulphation is 58%, on an anhydrous basis.

6. The method according to claim 1, wherein the inulin sulphate is partially hydrolysed.

7. The method according to claim 1, wherein the inulin sulphate is inulin polysulphate.

8. The method according to claim 7, wherein the inulin polysulphate is inulin polysulphate sodium salt.

9. The method according to claim 5, wherein the inulin sulphate sodium salt is inulin polysulphate sodium salt.

10. A method for the treatment of osteoarthritis, comprising administering orally to a mammal in need thereof a therapeutically effective amount of a sulphated oligosaccharide in acid form or as a physiologically acceptable salt thereof, derived from inulin.

11. The method according to claim 10, wherein the sulphated oligosaccharide is a polysulphated oligosaccharide.

* * * * *